US012716833B2

(12) United States Patent
Ehlers et al.

(10) Patent No.: US 12,716,833 B2
(45) Date of Patent: Aug. 25, 2026

(54) SPECTROMETRIC MEASUREMENT METHOD

(71) Applicant: Endress+Hauser Optical Analysis, Inc., Ann Arbor, MI (US)

(72) Inventors: Patrick Ehlers, Mölnlycke (SE); Randy Benedict, Ann Arbor, MI (US); Florian Krogmann, Kreuzlingen (CH); Joseph B. Slater, Dexter, MI (US); Joel Patrow, Ann Arbor, MI (US); Oliver Link, Gundelfingen (DE); Jürgen Dessecker, Wittlingen (DE)

(73) Assignee: Endress+Hauser Optical Analysis, Inc., Ann Arbor, MI (US)

( * ) Notice: Subject to any disclaimer, the term of this patent is extended or adjusted under 35 U.S.C. 154(b) by 151 days.

(21) Appl. No.: 18/819,889

(22) Filed: Aug. 29, 2024

(65) Prior Publication Data

US 2026/0063537 A1 Mar. 5, 2026

(51) Int. Cl.
*G01N 21/31* (2006.01)
*G01N 33/483* (2006.01)
*G06N 3/096* (2023.01)

(52) U.S. Cl.
CPC ......... *G01N 21/31* (2013.01); *G01N 33/4833* (2013.01); *G06N 3/096* (2023.01); *G01N 2021/3196* (2013.01); *G01N 2201/1293* (2013.01); *G01N 2201/1296* (2013.01)

(58) Field of Classification Search
CPC ...... G01J 3/50; G01J 3/40; G01J 3/462; G01J 3/504; G01J 2003/466; G01J 3/463
See application file for complete search history.

(56) References Cited

U.S. PATENT DOCUMENTS

2023/0304860 A1* 9/2023 Sabry .................... G16C 20/70
2026/0056054 A1* 2/2026 Guzzonato ............ G01J 3/0208

FOREIGN PATENT DOCUMENTS

DE 102022130045 A1 5/2024
DE 102024107007 A1 9/2025
EP 4063831 A1 9/2022
WO 2024046603 A1 3/2024

* cited by examiner

*Primary Examiner* — Hwa Andrew Lee
(74) *Attorney, Agent, or Firm* — Gil M. Repa; Endress+Hauser (USA) Holding, Inc.

(57) ABSTRACT

A spectrometric measurement method of, in measurement situation(s) within a predetermined application, determining measurement results of measurand(s) of a medium of an application specific type, wherein each measurement situation is predetermined by specifying at least one influencing factor affecting measured spectra in the respective measurement situation, includes: based on universal training data, determining a universal model for determining predictions of each measurand; for each measurement situation, based on the universal model and supplementary training data including at least one supplementary spectrum determined in the respective measurement situation and corresponding supplementary value(s) of each measurand, determining a dedicated model for determining measurement results of each measurand in the respective measurement situation; and based on measured spectra determined in the respective measurement situation and the dedicated model, determining measurement results of each measurand of the medium.

20 Claims, 2 Drawing Sheets

SPECTROMETRIC MEASUREMENT METHOD

TECHNICAL FIELD

The present disclosure relates to a spectrometric measurement method of, in a predetermined application with spectrometers of a predetermined type, determining measurement results of at least one measurand of a medium of an application-specific type.

BACKGROUND

Spectrometers of various types are currently employed in a large variety of different applications including industrial applications, e.g., applications in the chemical industry, in the pharmaceutical industry and in the oil and gas industry, as well as in biotechnological and laboratory applications to determine and to provide measurement results of various measurands. As an example, Raman spectrometers are, e.g., employed to determine a concentration of at least one component included in the medium, e.g., a methane concentration and/or an ethane concentration included in a liquid natural gas, and/or at least one other measurand of the medium. As another example, absorption spectrometers measuring absorption are, e.g., employed to determine a concentration of at least one component included in the medium in various different applications.

Spectrometers commonly include a light source transmitting light to a sample of the medium and a spectrometric unit receiving measurement light resulting from an interaction of the transmitted light with the medium and providing raw spectra of the received measurement light. The raw spectra are commonly provided to a signal processor determining measured spectra based on the raw spectra and an algorithm for determining spectral values of the measured spectra based on spectral values of the raw spectra. The measured spectra are, e.g., provided to an evaluation unit determining measurement results of the measurand(s) based on a previously determined model for determining the measurement results based on spectral values of the measured spectra.

Models used in spectroscopy for determining measurement results of measurands are commonly determined based on a detailed mathematical analysis of training data including experimentally determined reference spectra of reference samples of the medium exhibiting known reference values of the measurand. The determination of these models is, however, a laborious and time consuming process, in particular because of the considerable number of reference spectra required, the complexity of interdependencies between spectral values of the reference spectra and the reference values of the measurand, and/or because of influences of application specific properties affecting the spectral values and/or the spectral distribution of the reference spectra.

Correspondingly, there is a desire to use the same model on multiple spectrometers at multiple measurement sites in the same application.

Different spectrometers do, however, exhibit different measurement properties. Even though some progress has been achieved in calibrating spectrometers, in particular in calibrating the spectral responsivity of spectrometers, there still remains a certain variability associated with the technical properties of different spectrometers of the same type. This adverse effect is especially large for Raman spectrometers because variations of the technical properties of Raman spectrometers have a large impact due to the extremely low signal to noise ratio inherent to Raman spectroscopic measurements caused by the notoriously low intensity of Raman scattered light.

In addition, spectrometric measurements performed at different measurement sites within a predetermined application specified by the measurand(s) to be measured and the medium of the application-specific type may be affected by a wide range of further influencing factors. These influencing factors, e.g., include influencing factors associated with the technical properties of the spectrometers, influencing factors associated with the measurement set-up, influencing factors associated with processes performed at the measurement sites, influencing factors associated with measurement conditions, and/or influencing factors associated with properties of the medium of the application-specific type prevailing at the different measurement sites within the same application. As an example, the measurement set-up, the measurement conditions, and/or the composition of a liquid natural gas prevailing at a liquid natural gas production facility may differ from the measurement set-up and/or the composition of a liquid natural gas prevailing at a liquid natural gas refrigeration facility.

As a result, measured spectra of the medium determined by different spectrometers at different measurement sites within in the same application exhibit a variability due to variations of the influencing factors affecting the measurements at the different measurement sites.

Consequently, measurement results determined with the same model based on measured spectra determined by different spectrometers of the same type installed at different measurement sites within the same application will exhibit a measurement error caused by the variability of the measured spectra.

This measurement error can be reduced to a certain extend by determining the model based on training data covering at least some of the variations of at least some of the known influencing factors that may occur within a predetermined application. This does, however, lead to a significant increase of the time and effort involved in determining and providing the training data for determining the model. In addition, in practice it is neither possible nor economical to determine and to provide training data covering variations of all possible present and future influencing factors that may need to be taken into account for the given predetermined application. Thus, even if the model is determined based on training data accounting for some of the variations, measurement results determined with this model will still exhibit a measurement error due to the remaining variabilities that are not accounted for in the training data.

Accordingly, there remains a need for further contributions in this area of technology.

As an example, there is a need for a spectrometric measurement method of, with spectrometers of a predetermined type, determining measurement results of at least one measurand of a medium of an application-specific type in multiple different measurement situations within in a predetermined application that enables a more efficient and more accurate determination of the measurement results in each measurement situation.

As another example, there is a need for a spectrometric measurement method that is better suited to cope with the variability exhibited by measured spectra of the medium determined by spectrometers in different measurement situations within a predetermined application.

SUMMARY

The present disclosure includes a spectrometric measurement method of in one measurement situation or in multiple different measurement situations within a predetermined application with at least one spectrometer of a predetermined type determining measurement results of at least one measurand of a medium of an application specific type, wherein each measurement situation is predetermined by specifying at least one influencing factor affecting measured spectra determined by the spectrometer(s) in the respective measurement situation; the method comprising:

performing reference measurements by with at least one spectrometer determining reference spectra of reference samples of the medium, and for each reference sample determining and/or providing a reference value of each measurand of the reference sample;

based on universal training data including the reference spectra and the corresponding reference values determining a universal model for determining predictions of each measurand based on measured spectra of the medium determined by spectrometers in the predetermined application; and for each measurement situation performing the method steps of:

in the respective measurement situation with at least one spectrometer determining and providing measured spectra of the medium;

for at least one supplementary spectrum or a limited number of supplementary spectra, wherein each supplementary spectrum is given by one of the measured spectra determined by the spectrometer(s) employed in the respective measurement situation, determining and/or providing a supplementary value of each measurand of the medium;

based on the universal model and supplementary training data including at least one or each supplementary spectrum and the corresponding supplementary value(s) determining a dedicated model for determining measurement results of each measurand based on measured spectra of the medium determined and provided by the spectrometer(s) employed in the respective measurement situation; and based on measured spectra of the medium determined and provided by the spectrometer(s) employed in the respective measurement situation and the dedicated model determining and providing measurement results of each measurand of the medium.

The method provides the advantage that it enables a more efficient and more accurate determination of measurement results of each measurand of the medium in each predetermined measurement situation within the predetermined application.

In this respect, the universal model provides the advantage that it accounts for the application-specific interrelations between spectral values of measured spectra and the measurand(s) in the predetermined application. In addition, the supplementary spectra and the corresponding supplementary values of each measurand determined for each measurement situation provide the advantage that they reflect the impact of characteristics of the respective measurement situation on measured spectra determined in the respective measurement situation.

The universal model already accounting for the application-specific interrelations provides the advantage that determining the dedicated models based on the universal model and the supplementary training data is significantly less complex and less demanding than the determination of the universal model. This provides the advantage that only a small number of supplementary spectra and corresponding supplementary values is needed to determine the dedicated model for each measurement situation such that the impact of characteristics the respective measurement situation on measured spectra determined in the respective measurement situation is properly accounted for.

For each measurement situation determining and subsequently employing the dedicated model provides the advantage that based on the dedicated model a high measurement accuracy is achieved without requiring the universal model to be determined based on universal training data covering the full range of variability of measured spectra that may occur within the predetermined application. This reduces the time and effort involved in determining the universal training data for determining universal model. At the same time, measurement results determined with the dedicated models each accounting for the impact of characteristics of the respective measurement situation on measured spectra determined in the respective measurement situation are significantly more accurate than predictions of the measurand(s) determined with the universal model in the respective measurement situation.

In certain embodiments, each dedicated model is determined such, that measurement results of each measurand determined with the dedicated model based on the or each supplementary spectrum correspond to the supplementary value of the respective measurand exhibited by the medium during the determination of the respective supplementary spectrum.

According to a first embodiment, for at least one or each measurement situation determining the dedicated model is performed by based on the universal model and the supplementary training data retraining the universal model under consideration of the supplementary training data and determining the dedicated model to be given by the retrained universal model.

In certain embodiments of the first embodiment, retraining the universal model is performed in the same manner as the training of the universal model and/or based on the same underlying algorithm that has previously been employed to determine the universal model, and/or includes strengthening an impact of circumstances prevailing in the respective measurement situation on the retrained universal model by assigning a larger weight to the supplementary training data than to the universal training data.

According to a second embodiment, for at least one or each measurement site determining the dedicated model is performed by based on the supplementary training data adjusting the universal model such, that measurement results of each measurand determined with the adjusted universal model based on the supplementary spectra correspond to the supplementary values of the respective measurand exhibited by the medium during the determination of the respective supplementary spectrum, and determining the dedicated model to be given by the adjusted universal model.

In certain embodiments of the second embodiment, adjusting the universal model is performed by based on each supplementary spectrum with the universal model determining the prediction of each measurand, based on the predictions determined based on the supplementary spectra and the corresponding supplementary values determining prediction errors exhibited by the predictions, and performing at least one of:

a) based on the prediction errors adjusting the universal model such, that prediction errors of predictions determined with the adjusted universal model based on the supplementary spectra are minimized;
b) performing an iterative process of based on the prediction errors adjusting the universal model and repeating the method steps of based on each supplementary spectrum with the adjusted universal model determining the prediction of each measurand, determining prediction errors exhibited by these predictions and subsequently adjusting the previously adjusted universal model until the prediction errors of predictions determined with the resulting adjusted universal model decrease below a predetermined threshold; and c) adjusting the universal model by adjusting at least one weighing factor, at least one parameter, a filter, a smoothing algorithm and/or at least one other model component of the universal model such, that deviations between predictions determined with the adjusted universal model based on the supplementary spectra and the corresponding supplementary values are minimized.

According to a third embodiment, for at least one or each measurement site the dedicated model is determined as a model given by the universal model determining predictions of each measurand based on measured spectra determined by the spectrometer(s) employed in the respective measurement situation and a transformer determining measurement results of the measurand(s) based on the predictions determined with universal model; and determining the dedicated model includes:

based on at least one or each supplementary spectrum with the universal model determining the corresponding prediction of each measurand; and based on the prediction(s) determined based on the or each supplementary spectrum and the corresponding supplementary value(s) determining the transformer such, that the measurement result of each measurand determined with the transformer based on the prediction(s) determined with the universal model based on the or each supplementary spectrum corresponds to the corresponding supplementary value of the respective measurand exhibited by the medium during determination of the respective supplementary spectrum.

In certain embodiments of the third embodiment, for at least one or each measurement site determining the transformer is performed by for each measurand determining a transfer function for calculating measurement results of the respective measurand as a function, as a linear function, a polynomial function of a given order, or another mathematical function of the prediction of the respective measurand and a set of at least one parameter; wherein for each measurand the at least one parameter of the transfer function is determined by fitting the respective transfer function to a set of data points, each data point is given by one of the predictions of the respective measurand determined with the universal model based on one of the supplementary spectra and the corresponding supplementary value, and the set of data points consists of a single data point, of two data points, of a limited number of data points smaller or equal to 20, smaller or equal 10 or even smaller or equal 5 data points, or of multiple data points.

In a fourth embodiment, given by a further embodiment of the third embodiment, for at least one or each measurement site the transformer included in the dedicated model is determined in form of a transfer model for determining measurement results of the measurand(s) based on predictions determined with the universal model based on measured spectra determined by the spectrometer(s) employed in the respective measurement situation, and determining the respective dedicated model includes based on transfer model training data including predictions of the measurands determined with the universal model based on the supplementary spectra and the corresponding supplementary value(s) of each measurand determining and providing the transfer model.

In certain embodiments of the fourth embodiment, for at least one or each measurement site determining the transfer model either includes performing at least one of the method steps of:

a) based on a detailed analysis of the transfer model training data determining and providing an algorithm for calculating the measurement results of each measurand based on predictions of the measurand(s) determined with the universal model based on measured spectra determined by the spectrometer(s) employed in the respective measurement situation, and b) based on the transfer model training data performing a multivariate analysis, a partial least squares regression, a support vector regression and/or a principal component analysis of the predictions and/or a method step of quantitatively assessing interdependencies between the predictions of the measurands and the corresponding supplementary values of each measurand; or includes based on the transfer model training data training a neural network to determine the measurement results of the measurand(s) based on predictions determined with the universal model based on measured spectra determined in the respective measurement situation and determining the transfer model to be given by the trained neural network.

In further embodiments of the fourth embodiment, for at least one or each measurement situation the transfer model is determined based on supplementary training data including a limited number smaller or equal to 100, smaller or equal to 50 or even smaller or equal to 20 of supplementary spectra and the corresponding supplementary values.

In a fifth embodiments, for at least one or each measurement site the dedicated model is determined as a model given by an adapted universal model determining adapted predictions of each measurand based on measured spectra determined in the respective measurement situation and an adapted transformer determining the measurement results of the measurand(s) based on adapted predictions determined with the adapted universal model based on measured spectra determined in the respective measurement situation; and determining the dedicated model includes:

based on the universal model and the supplementary training data retraining the universal model under consideration of the supplementary training data and determining the adapted universal model to be given by the retrained universal model;

based on at least one or each supplementary spectrum with the adapted universal model determining the adapted prediction of each measurand; and based on the adapted prediction(s) determined with the adapted universal model based on the or each supplementary spectrum and the corresponding supplementary value(s) determining the adapted transformer such, that the measurement result of each measurand determined with the adapted transformer based on the adapted prediction(s) determined with the adapted universal model based on the or each supplementary spectrum corresponds to the supplementary value of the respective measurand exhibited by the medium during the determination of the respective supplementary spectrum.

In certain embodiments of the fifth embodiment, determining the adapted universal model is performed by retraining of the universal model in the same manner as the training of the universal model and/or based on the same underlying algorithm that has previously been employed to determine the universal model, and/or in a manner preserving a global validity of the retrained universal model by assigning a smaller weight to the supplementary training data than to the universal training data.

In further embodiments of the fifth embodiment, determining the adapted transformer includes for each measurand determining an adapted transfer function for calculating measurement results of the respective measurand as a function, as a linear function, a polynomial function of a given order, or another mathematical function of the adapted prediction of the respective measurand and a set of at least one parameter, wherein for each measurand the at least one parameter of the adapted transfer function is determined by fitting the respective adapted transfer function to a set of at least one or multiple data points, wherein each data point is given by one of the adapted predictions of the respective measurand determined with the adapted universal model based on one of the supplementary spectra and the corresponding supplementary value.

According to a sixth embodiment, given by a further embodiment of the fifth embodiment, for at least one or each measurement site the adapted transformer is determined in form of an adapted transfer model for determining measurement results of the measurand(s) based on adapted predictions of the measurand(s) determined with the adapted universal model based on measured spectra determined in the respective measurement situation, and the adapted transfer model is determined based on transfer model training data including the adapted predictions of the measurand(s) determined with the adapted universal model based on the supplementary spectra and the corresponding supplementary values.

In certain embodiment of the sixth embodiment, determining the adapted transfer model either includes performing at least one of the method steps of:

a) based on a detailed analysis of the transfer model training data determining and providing an algorithm for calculating measurement results of each measurand based on adapted predictions of the measurand(s) determined with the adapted universal model based on measured spectra determined in the respective measurement situation, and b) performing a multivariate analysis, a partial least squares regression, a support vector regression and/or a principal component analysis of the adapted predictions and/or a method step of quantitatively assessing interdependencies between the adapted predictions of the measurand(s) and the corresponding supplementary values of each measurand; or includes based on the transfer model training data training a neural network to determine the measurement results of the measurand(s) based on the adapted predictions determined with the adapted universal model based on the measured spectra determined in the respective measurement situation and determining the adapted transfer model to be given by the trained neural network.

In further embodiments of the sixth embodiments, for at least one or each measurement situation specifying the at least one influencing factor includes performing at least one of: specifying at least one influencing factor associated with a measurement set-up; specifying the measurements to be performed on samples of the medium or to be in situ measurements; specifying the measurements to be performed in a flowcell conducting the medium or a in container, a bioreactor or another type of vessel containing the medium; specifying at least one influencing factor associated with measurement conditions; specifying a parameter range for at least one parameter and/or a temperature; specifying at least one influencing factor associated with the medium of the application-specific type within the respective measurement situation; specifying at least one property of the medium; specifying the medium to being subjected to a specified process, a specified production process and/or a specified processing procedure; specifying a facility containing and/or processing the medium; specifying the medium to include at least one specified component, to include multiple specified components, or to consist of specified components; specifying the specific spectrometer performing the measurements; and/or specifying the specific measurement site where the measurements are performed.

In certain embodiments, the predetermined application is a biotechnological application, wherein mammalian cells producing an active component of a drug are grown in a cell culture medium, and at least one measurement situation is predetermined by specifying or by solely specifying the type of the cell culture medium and/or the type of the mammalian cells.

In further embodiments, the method further comprises for at least one or each measurement situation performing the method steps of based on the supplementary training data and the dedicated model determining a measurement accuracy of measurement results determined with the dedicated model, and performing at least one of:

a) providing the measurement accuracy; and b) in case the measurement accuracy is lower than a predetermined minimum accuracy performing at least one:

b1) determining additional supplementary training data, redetermining the dedicated model based on the supplementary training data and the additional supplementary training data and determining the dedicated model to be given by the redetermined dedicated model, and b2) limiting the respective measurement situation to be given by a limited measurement situation predetermined by specifying at least one additional influencing factor affecting measured spectra determined by the spectrometer(s) in the respective measurement situation, and based on the universal model and supplementary training data determined in the limited measurement situation determining the dedicated model for determining measurement results of each measurand based on measured spectra of the medium determined and provided by the spectrometer(s) employed in the limited measurement situation.

In certain embodiments, the method further comprises at least once performing the method steps of updating the universal model based on the universal training data and the supplementary training data that has previously been determined for at least one measurement situation; and subsequently for at least one measurement situation determining the corresponding dedicated model based on the updated universal model.

BRIEF DESCRIPTION OF THE DRAWINGS

The described embodiments and other features, advantages and disclosures contained herein, and the manner of attaining them, will become apparent and the present disclosure will be better understood by reference to the following description of various embodiments of the present disclosure taken in junction with the accompanying drawings, wherein.

DETAILED DESCRIPTION

The present disclosure includes a spectrometric measurement method of, in at least one measurement situation or in multiple different measurement situations within a predetermined application, with at least one spectrometer of a predetermined type, determining measurement results MR of at least one measurand of a medium of an application-specific type.

Figure 1:
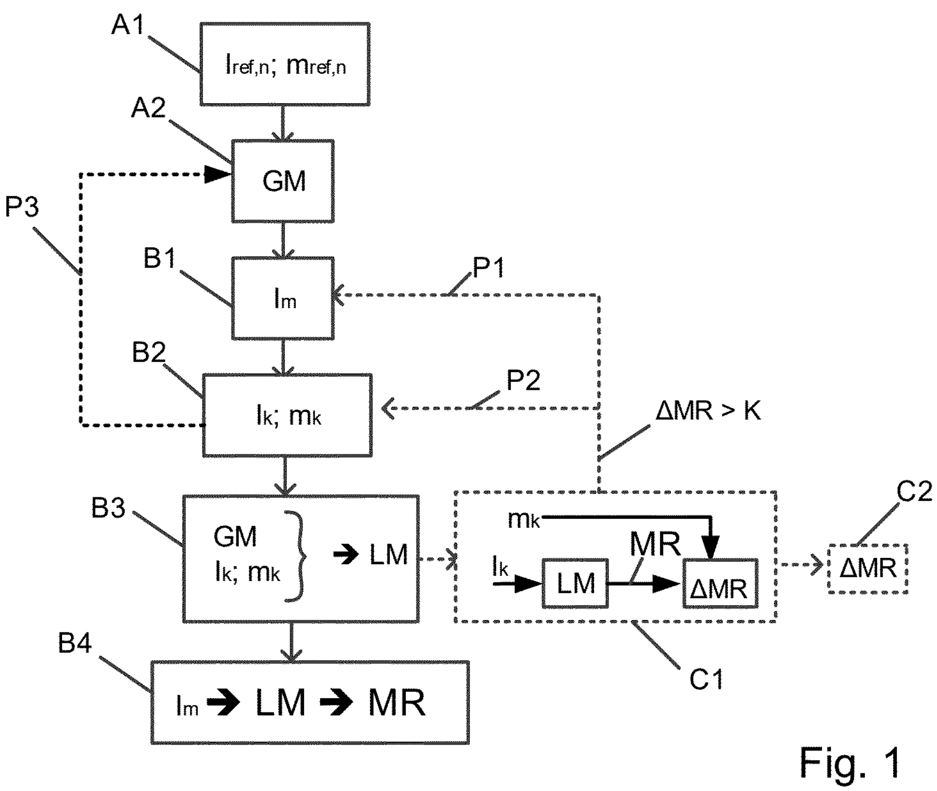
FIG. 1 shows a flow chart of a spectrometric measurement method according to the present disclosure.

A flow chart of the spectrometric measurement method is shown in FIG. 1.

With respect to the method shown in FIG. 1, the predetermined application is, e.g., a specific process in the life science industry, in the pharmaceutical industry, in biotechnology, in the oil and gas industry, in the chemical industry, in the food and beverage industry, or in a process of another field.

In certain embodiments, the predetermined application is, e.g., specified by the measurand(s) to be measured and the application-specific type of the medium. Depending on the predetermined application, the at least one measurand, e.g., include(s) a concentration of at least one component included in the medium, a pH-value of the medium, a melt index of the medium, a cell motility of the medium, and/or at least one other property of the medium.

In certain embodiments, the predetermined application is, e.g., a liquid natural gas (LNG) application. In such a case, media of the application-specific type are liquid natural gases and the measurand(s), e.g., include the concentration of at least at least one component, e.g., methane ($CH_4$) and/or ethane ($C_2H_6$), included in the liquid natural gas.

In other embodiments, the predetermined application is, e.g., a biotechnological application, wherein mammalian cells producing an active component of a drug are grown in a cell culture medium. In such a case, media of the application-specific type are, e.g., cell culture media including mammalian cells and the measurand(s), e.g., include a glucose concentration, a lactate concentration, a viable cell density of the mammalian cells contained in the cell culture medium, and/or at least one other property of the medium.

In the method according to the present disclosure disclosed herein, each measurement situation is predetermined by specifying at least one influencing factor affecting measured spectra determined by the spectrometer(s) employed in the respective measurement situation. For each measurement situation, specifying at least one influencing factor, e.g., includes specifying at least one influencing factor associated with the measurement set-up, at least one influencing factor associated with the measurement conditions, and/or at least one influencing factor associated with the medium of the application-specific type within the respective measurement situation.

As an example, with respect to the measurement set-up, a particular measurement situation may, e.g., be predetermined to be limited to measurements performed on samples of the medium, to in situ measurements, e.g., to measurements performed in a flowcell conducting the medium or a in container, e.g., a bioreactor or another type of vessel, containing the medium. In addition or as an alternative, a particular measurement situation may, e.g., be predetermined to be limited to measurements performed with specified equipment, e.g., a specific type of optical system, specified for the respective measurement situation.

As another example, with respect to the measurement conditions, a particular measurement situation may, e.g., be predetermined to be limited measurements performed in a specified parameter range of at least one parameter, e.g., a specified temperature range.

As another example, with respect to the measurement conditions and/or the properties of the medium, a particular measurement situation may, e.g., be predetermined to be limited to measurements of the medium being subjected to a specified process, e.g., a specified production and/or processing procedure, and/or predetermined to be limited measurements of the medium performed on specified facilities containing and/or processing the medium. As an example, in context with the liquid natural gas application mentioned above, a particular measurement situation may, e.g., be predetermined to be limited measurements performed on liquid natural gas production facilities, on liquid natural gas processing facilities, on liquid natural gas refrigeration facilities, or on liquid natural gas storage facilities.

As another example, with respect to the properties of the medium, a particular measurement situation may, e.g., be predetermined to be limited to measurements on media of the application-specific type including at least one specified component, including multiple specified components, or consisting of specified components.

As an example, in context with the biotechnological application mentioned above, a particular measurement situation may, e.g., be predetermined to be limited to measurements performed on media of the application-specific type including a specified cell culture medium, e.g., a cell culture medium provided by a specific manufacturer, and/or including mammalian cells of a specific type, e.g., hamster ovary cells, human embryonic kidney cells, or mammalian cells of another type.

For each measurement situation, the flexibility given by the type and/or the number of influencing factors specified, as well as the degree of preciseness of their specification may be used in various ways.

In certain embodiments, at least one or each measurement situation is, e.g., predetermined in a restrictive manner. This provides the advantage that it leads to a corresponding restriction of variations exhibit by measured spectra determined in the restrictively predetermined measurement situation. A relatively restrictive predetermination of a measurement situation leading to a correspondingly large limitation of variations exhibited by the measured spectra is, e.g., achieved by specifying the specific spectrometer determining the measured spectra and/or the specific measurement site where the spectrometric measurements are performed. Correspondingly, in certain embodiments, at least one or each measurement situation is, e.g., predetermined by specifying the specific spectrometer determining the measured spectra and/or the specific measurement site where the spectrometric measurements are performed.

In addition or as an alternative, in certain embodiments, at least one or each measurement situation is, e.g., predetermined in a broader manner. This provides the advantage that it increases the number of measurement sites where the respective measurement situation occurs. As an example, in context with the biotechnological application mentioned above, at least one measurement situation may, e.g., be predetermined in a broader manner by solely specifying the specific cell culture medium, and/or the specific type of the mammalian cells included in the cell culture medium. In addition or as an alternative, at least one measurement situation within this biotechnological application may, e.g., be predetermined in a more restrictive manner, e.g., as outlined above.

As shown in FIG. 1, the method according to the present disclosure includes a method step A1 of performing reference measurements by, with at least one spectrometer 100, determining reference spectra $I_{ref,n}$ of multiple reference samples of the medium of the application-specific type and, for each reference sample, determining and/or providing a reference value $m_{ref,n}$ of each measurand of the reference sample.

The reference measurements are, e.g., performed such that universal training data including the reference spectra $I_{ref,n}$ and the corresponding reference values $m_{ref,n}$ of each measurand reflects the application-specific interrelation between spectral values of measured spectra $I_m$ of the medium and the measurand(s) within a predetermined measurement range.

As an example, in context with the liquid natural gas application mentioned above, the reference samples, e.g., include samples covering a range of methane concentrations and/or a range of ethane concentrations. In certain embodiments, these reference samples, e.g., include samples covering a range of different compositions of the liquid natural gas.

As a further example, in context with the biotechnological application mentioned above, the reference samples, e.g., include samples covering a range of glucose concentrations, a range of lactate concentrations, and/or a range of viable cell densities. In certain embodiments, these reference samples, e.g., include samples covering a range of different compositions the cell culture medium and/or covering a range of different types of mammalian cells.

The or each spectrometer 100 employed to perform the reference measurements is preferably of the same type as the spectrometer(s) 100 employed in each measurement situation.

Figure 2:
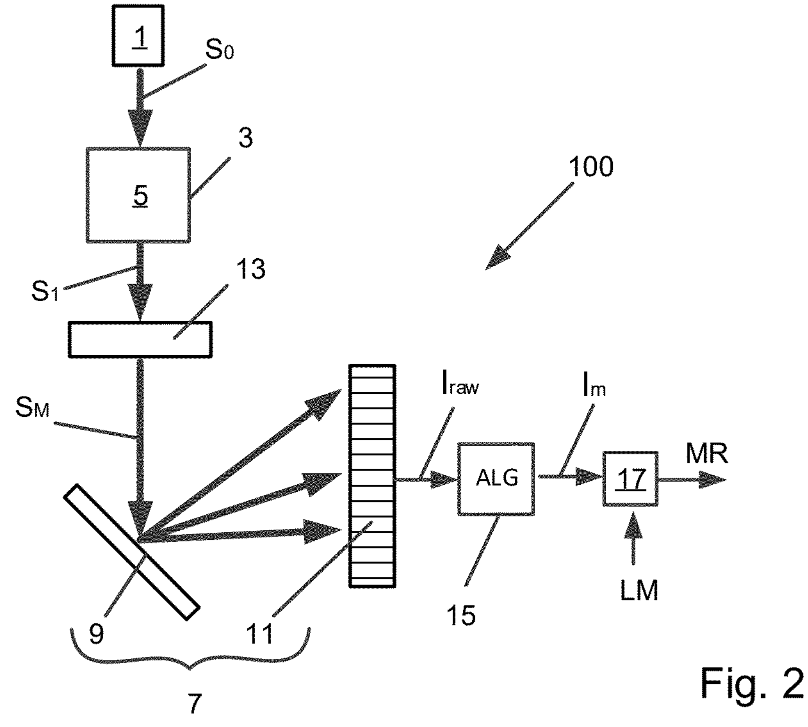
FIG. 2 shows a schematic of a spectrometer.

An exemplary embodiment of a spectrometer 100 of the predetermined type is shown in FIG. 2. The exemplary spectrometer 100 shown includes a light source 1 transmitting light $S_0$ to a measurement region 3 configured to accommodate a sample 5 of the medium and a spectrometric unit 7 configured to receive measurement light $S_M$ resulting from an interaction of the transmitted light $S_0$ with the medium and configured to determine and to provide raw spectra $I_{raw}$ of the received measurement light $S_M$.

In certain embodiments, the spectrometric unit 7, e.g., includes a disperser 9, e.g., a diffractive or holographic grating, dispersing the incident measurement light $S_M$, and a detector 11 receiving the dispersed measurement light $S_M$. In certain embodiments, the detector 11, e.g., includes an array of detection elements, e.g., an array of charge coupled devices (CCD) or an array of photodiodes, each receiving a fraction of the dispersed light and determining and providing a detector signal corresponding to an intensity of the fraction of the dispersed light received by the respective detector element. In these embodiments, the raw spectra $I_{raw}$ are, e.g., provided by the spectrometric unit 7 in the form of the detector signals provided by the individual detector elements.

With respect to the predetermined type of spectrometer 100 used throughout the method shown in FIG. 1, each spectrometer 100 is, e.g., given by a Raman spectrometer. In this case, the light source 1 of each spectrometer 100 is e.g., a monochromatic light source, e.g., a laser, configured to transmit excitation light $S_0$ having a predetermined excitation wavelength, e.g., a wavelength in the visual or near infrared wavelengths range. In certain embodiments, each Raman spectrometer e.g., includes a filter 13, e.g., a notch-filter, configured to receive light $S_1$ emanating from the illuminated sample 5 and to provide measurement light $S_M$ including Raman scattered light emanating from the illuminated sample 5 to the spectrometric unit 7. In addition or as an alternative, the spectrometric unit 7 of each Raman spectrometer is e.g., configured to determine and to provide the measured spectra $I_m$ as intensity spectra representing the spectral intensities of the Raman scattered light emanating from the illuminated sample 5 in a predetermined spectral range, e.g., a wavelength range or a wavenumber range.

As an alternative, in certain embodiments, the spectrometers 100 of the predetermined type employed throughout the method shown in FIG. 1 are, e.g., given by absorption spectrometers. In such an embodiment, the light source 1 is, e.g., a broad band light source transmitting light $S_0$ having a broad spectral range through the sample 5 accommodated in the measurement region 3, e.g., light $S_0$ including wavelengths in the visual, ultraviolet and/or infrared range. In these embodiments, the measured spectra $I_m$of the measurement light LM exiting the measurement region 3 are, e.g., determined as absorption spectra representing the spectral absorption of the medium as a function of the spectral line or as intensity spectra representing spectral intensity values of the measurement light $S_M$.

As a further alternative, the spectrometers 100 of the predetermined type used in method shown in FIG. 1 are, e.g., each given by a dispersive spectrometer, by tunable diode laser spectrometer, or by another type of spectrometer.

Regardless of the type of the spectrometers 100 used, each spectrometer 100, e.g., includes a signal processor 15, e.g., a computer, a microprocessor or another type of calculating unit, connected to and/or communication with the spectrometric unit 7 and configured to determine and to provide measured spectra $I_m$ of the medium based on the raw spectra $I_{raw}$ provided by the spectrometric unit 7. Determining the measured spectra $I_m$ is, e.g., performed by the signal processor 15 based on an algorithm ALG for determining the spectral values of the measured spectra $I_m$ based on the spectral values of the raw spectra $I_{raw}$ provided by the spectrometric unit 7. The algorithm ALG is, e.g., implemented in each spectrometer 100 of the given type by the manufacturer.

The spectrometers 100 employed in the method according to the present disclosure shown in FIG. 1 are preferably calibrated before they are put into operation. To this extent calibration, methods known in the art, including methods of calibrating a spectral axis and/or a spectral responsivity, are, e.g., employed and the algorithm ALG for determining the spectral values of the measured spectra $I_m$ is adjusted and/or amended accordingly.

Following the reference measurements, the method further includes a method step A2 of, based on universal training data including the reference spectra $I_{ref,n}$ and the corresponding reference values $m_{ref,n}$, determining an application-specific universal model GM for determining predictions MP of each measurand based on measured spectra $I_m$ of the medium determined by spectrometers 100 of the predetermined type in the predetermined application.

With respect to the determination of the universal model GM determination, methods employed in the prior art to determine models based on reference spectra and corresponding reference values of the measurand(s) may be used. As an example, in certain embodiments, the universal model GM is, e.g., trained based on the universal training data including the reference spectra $I_{ref,n}$, and the corresponding reference values $m_{ref,n}$. Training the universal model GM is, e.g., performed by, based on a detailed analysis of the universal training data, determining and providing an algorithm for calculating predictions MP of each measurand based on spectral values of measured spectra $I_m$ of the medium. In certain embodiments, the analysis of the universal training data and/or the determination of the universal model GM, e.g., includes performing a multivariate analysis, a partial least squares regression, a support vector regression, and/or a principal component analysis of the universal training data and/or a method step of quantitatively assessing interdependencies between spectral values of the reference spectra $I_{ref,n}$ and the corresponding reference values $m_{ref,n}$ of each measurand.

As an alternative, in certain embodiments, determining the universal model GM, e.g., includes training a neural network to determine predictions MP of each measurand based on measured spectra $I_m$ of the medium. In these embodiments, the trained neural network is subsequently employed as the universal model GM.

Following the preparatory method steps A1 and A2, the method further includes a sequence of method steps B1, B2, B3 and B4 that are performed for each measurement situation.

The sequence includes a method step B1 of, in the respective measurement situation with at least one spectrometer 100 employed in the respective measurement situation, determining and providing measured spectra $I_m$ of the medium. Here, each spectrometer 100 performing the determination of measured spectra $I_m$ is of the same predetermined type as the spectrometer(s) 100 performing the reference measurements and preferably also calibrated as outlined above.

For each measurement situation, the determination of the measured spectra $I_m$ is, e.g., performed at one or multiple measurement sites fulfilling the specifications based on which the respective measurement situation has been predetermined. As an example, for each measurement situation predetermined by specifying the specific spectrometer 100 and the specific measurement site where this specific spectrometer 100 is installed, each measured spectrum $I_m$ is determined with this specific spectrometer 100 at this specific measurement site. As another example, in context of the biotechnological application mentioned above, for the or each measurement situation predetermined by solely specifying the specific cell culture medium, and/or the specific type of the mammalian cells included in the cell culture medium, the measured spectra $I_m$ are, e.g., determined by at least one or multiple spectrometer(s) 100 installed at one or multiple measurement site(s), where the medium of the application-specific type includes the specified cell culture medium and/or mammalian cells of the specified type.

The sequence further includes a method step B2 of, for at least one supplementary spectrum $I_k$. each given by one of the measured spectra $I_m$ determined by the spectrometer(s) 100 in the respective measurement situation, determining and/or providing a supplementary value $m_k$ of each measurand exhibited by the medium in the respective measurement situation during the determination of the respective supplementary spectrum $I_k$.

In certain embodiments, at least one or each supplementary value $m_k$ of at least one or each measurand is, e.g., determined by measurement. In this case, the measurement of at least one or each supplementary value $m_k$ is, e.g., performed on a sample of the medium taken at the measurement site at the time when the respective supplementary spectrum $I_k$ was determined. To this extent, highly accurate measurement devices and/or laboratory instruments are, e.g., employed to measure the supplementary values $m_k$ of each measurand of the samples. In addition or as an alternative, at least one or each supplementary value $m_k$ is, e.g., measured and provided by a measurement device, e.g., an in-line measurement device, measuring the respective measurand at the measurement site.

At certain measurement sites, the values of at least one or each measurand may be known during specific time periods, e.g., during specific operating phases and/or during specific stages of a process performed at the measurement site. In this case the supplementary spectra $I_k$, e.g., include at least one measured spectrum $I_m$ that has been determined during one of the specific time periods and the corresponding supplementary value(s) $m_k$ are given by the corresponding known value of the respective measurand.

Regardless of how the supplementary values $m_k$ of the measurand(s) are determined and/or provided, the thus determined supplementary training data, including at least one supplementary spectrum $I_k$ and the corresponding supplementary value(s) $m_k$ of each measurand, reflects the interrelation between measured spectra $I_m$ determined by the spectrometer(s) 100 in the respective measurement situation and the measurand(s) under the circumstances prevailing in the respective measurement situation. Correspondingly, for each measurement situation, the supplementary training data reflects the total impact of the or each specified influencing factor on measured spectra $I_m$ determined in the respective measurement situation. Depending on how restrictive the respective measurement situation has been predetermined, the circumstances accounted for in the supplementary training data, e.g., include characteristics associated with the measurement set-up, the measurement conditions, and/or the medium of the application-specific type within the respective measurement situation. For each measurement situation predetermined by specifying the specific spectrometer 100 and the specific measurement site, the supplementary training data reflects the impact of the technical properties of the specific spectrometer 100 determining the supplementary spectra $I_k$, the measurement set-up employed at the specified measurement site, the measurement conditions prevailing at the specified measurement site, and the properties of the medium prevailing at the respective measurement site.

Following the determination of the supplementary training data, the sequence further includes a method step B3 of, based on the application-specific universal model GM and the supplementary training data including at least one supplementary spectrum $I_k$ and the corresponding supplementary value(s) $m_k$ of each measurand, determining a dedicated model LM for determining measurement results MR of each measurand based on measured spectra $I_m$ of the medium determined and provided by the spectrometer(s) 100 employed in the respective measurement situation.

For each measurement situation, the dedicated model LM is preferably determined such that measurement results MR of each measurand determined with the dedicated model LM based on the supplementary spectra $I_k$ correspond to the supplementary values $m_k$ of the respective measurand exhibited by the medium during the determination of the respective supplementary spectrum $I_k$. This can be achieved in various ways.

As an example in certain embodiments, for at least one or each measurement situation determining, the corresponding dedicated model LM, e.g., includes, based on the universal model GM and the supplementary training data, adapting the universal model GM to the circumstances prevailing in the respective measurement situation. Exemplary embodiments of determining the dedicated model LM by adapting the universal model GM are shown in FIGS. 3 and 4.

Figure 3:
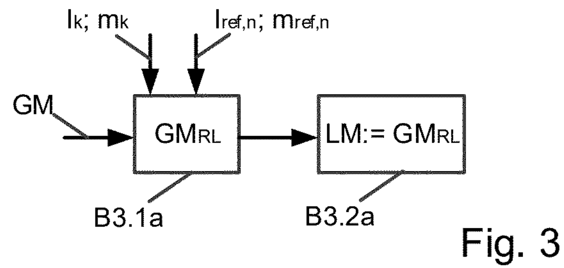
FIG. 3 shows a method of determining a dedicated model by retraining a universal model according to the present disclosure.
Figure 4:
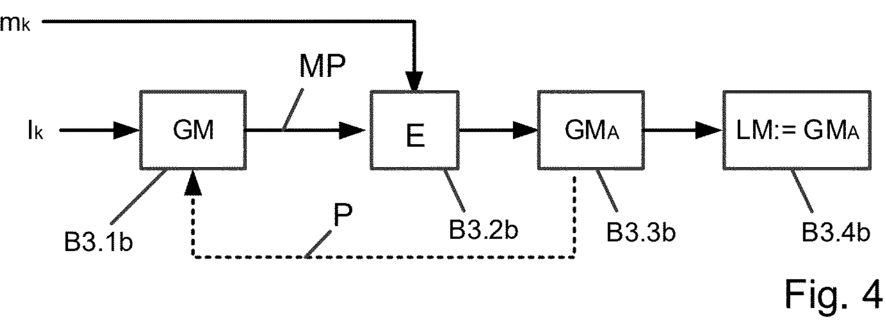
FIG. 4 shows a method of determining a dedicated model by adjusting a universal model according to the present disclosure.

In the embodiment shown in FIG. 3, the universal model GM is adapted to the circumstances prevailing in the respective measurement situation by, based on the universal model GM and the supplementary training data, performing a method step B3.1*a* of retraining the universal model GM under consideration of the supplementary training data and then a method step B3.2*a* of determining the dedicated model LM to be given by the retrained universal model $GM_{RL}$.

In certain embodiments, retraining the universal model GM to properly account for the circumstances prevailing in the respective measurement situation is, e.g., performed in the same manner as the initial training of the universal model GM and/or based on the same underlying algorithm that has previously been employed to determine the universal model GM. In that case, the initial training of the universal models GM and the retraining of the universal model GM differ in that the initial training is performed solely based on the universal training data, whereas the retraining is performed based on the universal training data and the supplementary training data.

Retraining the universal model GM under consideration of the supplementary training data provides the advantage that different weights can be assigned to the universal training data and the supplementary training data. As an example, in certain embodiments, retraining of the universal model GM is performed in a manner strengthening an impact of the circumstances prevailing in the respective measurement situation on the retrained universal model $GM_{RL}$ by assigning a larger weight to the supplementary training data, including the supplementary spectra $I_k$ and the corresponding supplementary values $m_k$, than to the universal training data including the reference spectra $I_{ref,n}$ and the corresponding reference values $m_{ref,n}$.

In the embodiment shown in FIG. 4, the universal model GM is adapted to the circumstances prevailing in the respective measurement situation by, based on the universal model GM and the supplementary training data, adjusting the universal model GM such that measurement results MR of each measurand determined with the adjusted universal model GMA based on the supplementary spectra $I_k$ correspond to the supplementary values $m_k$ of the respective measurand exhibited by the medium during the determination of the respective supplementary spectrum $I_k$.

In the exemplary embodiment shown in FIG. 4, determining the dedicated model LM, e.g., includes: a method step B3.1*b* of, based on each supplementary spectrum $I_k$, with the universal model GM determining the prediction MP of each measurand; a method step B3.2*b* of, based on the predictions MP determined based on the supplementary spectra $I_k$ and the corresponding supplementary values $m_k$, determining prediction errors E exhibited by the predictions MP; and a method step B3.3*b* of, based on the prediction errors E, adjusting the universal model GM such that the prediction errors E of predictions determined with the adjusted universal model $GM_A$ based on the supplementary spectra $I_k$ are minimized.

As indicated by the dotted arrow P shown in FIG. 4, in certain embodiments adjusting the universal model GM, e.g., includes an iterative process of, based on the prediction errors E determined in method step B3.2*b*, adjusting the universal model GM in method step B3.3*b* and repeating the method steps B3.1*b*, B3.2*b* and B3.3*b* based on the previously adjusted universal model by, with the previously adjusted universal model, determining predictions of each measurand, based on these predictions and the corresponding supplementary values $m_k$ determining prediction errors exhibited by these predictions, and subsequently adjusting the previously adjusted universal model until the prediction errors of predictions determined with the resulting adjusted universal model $GM_A$ decrease below a predetermined threshold.

In addition or as an alternative, in certain embodiments performing the adjustment of the universal model GM, e.g., includes adjusting at least one weighing factor, at least one parameter, a filter, a smoothing algorithm, and/or at least one other model component of the universal model GM such that deviations between the predictions MP determined with the adjusted universal model $GM_A$ based on the supplementary spectra $I_k$ and the corresponding supplementary values $m_k$ of the medium are minimized.

Following the adjustment of the universal model GM, the embodiment shown in FIG. 4 further includes a method step B3.4*b* of determining and providing the dedicated model LM given by the adjusted universal model $GM_A$.

In addition or as an alternative, in certain embodiments for at least one or each measurement situation the dedicated model LM, is e.g., determined as a model given by the universal model GM determining predictions MP of each measurand based on measured spectra $I_m$ determined by the spectrometer(s) 100 employed in the respective measurement situation and a transformer T determining the measurement results MR of the measurand(s) based on the predictions MP determined with the universal model GM in the respective measurement situation. In these embodiments, method step B3 of determining the dedicated model LM includes, based on the universal model GM and the supplementary training data, including at least one supplementary spectrum $I_k$ and the corresponding supplementary value $m_k$ of each measurand determining and providing the transformer T.

Figure 5:
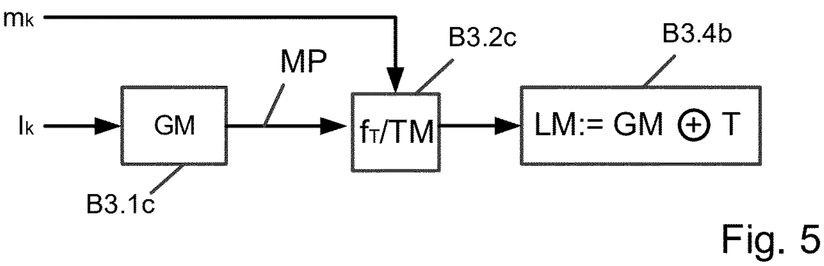
FIG. 5 shows a method of determining a dedicated model including a universal model and a transformer according to the present disclosure.

An exemplary embodiment of method step B3 including the determination of the transformer T is shown in FIG. 5. In this embodiment, determining the dedicated model LM includes a method step B3.1*c* of, based on at least one or each supplementary spectrum $I_k$, with the universal model GM determining the corresponding prediction MP of each measurand, and a method step B3.2*c* of, based on the prediction(s) MP determined based on the or each supplementary spectrum $I_k$ and the corresponding supplementary value(s) $m_k$ of the measurand(s), determining the transformer T such that the measurement result MR of each measurand determined with the transformer T based on the prediction(s) MP determined with the universal model GM based on the or each supplementary spectrum $I_k$ corresponds to the corresponding supplementary value $m_k$ of the respective measurand exhibited by the medium during determination of the respective supplementary spectrum $I_k$.

In certain embodiments, for at least one or each measurement situation determining the transformer T, e.g., includes for each measurand determining a transfer function $f_T$ for calculating measurement results MR of the respective measurand as a function of the prediction MP of the respective measurand and a set of at least one parameter. In this embodiment, the transfer function $f_T$ for each measurand is, e.g., determined as a linear function, a polynomial function of a given order, or another mathematical function for calculating measurement results MR of the respective measurand as a function of the prediction MP of the respective measurand and a set of at least one parameter. For each measurand the at least one parameter of the transfer function $f_T$ is, e.g., determined by fitting the respective transfer function $f_T$ to a set of at least one or multiple data points, wherein each data point is given by one of the predictions MP of the respective measurand determined with the universal model GM based on one of the supplementary spectra $I_k$ and the corresponding supplementary value $m_k$. To this extent, regression methods and/or polynomial fitting methods known in the art are, e.g., employed.

Determining the transformer T by determining the transfer function $f_T$ for each measurand provides the advantage that only a minimal amount of computing power is required, and very little supplementary training data is needed. As an example, measurement results MR determined with the dedicated model LM including the transformer T are already noticeably more accurate than the predictions MP determined with the universal model GM, when each transfer function $f_T$ of the transformer T is determined based on only a single data point and a significant increase of the measurement accuracy is already achieved when each transfer function $f_T$ of the transformer T is determined based two data points or a limited number of data points. Correspondingly, the transfer function $f_T$ for each measurand is, e.g., determined based on a set of data points consisting of single data point, of two data points, of a limited number of data points, e.g., a limited number smaller or equal to 20, smaller or equal to 10 or even smaller or equal to 5 data points, or of multiple data points.

In addition or as an alternative, in certain embodiments, for at least one or each measurement situation, the corresponding transformer T is, e.g., determined in form of a transfer model TM for determining the measurement results MR based on the predictions MP determined with the universal model GM based on measured spectra $I_m$ determined by the spectrometer(s) 100 employed in the respective measurement situation. This approach is especially favorable in embodiments of the method according to the present disclosure in which two or more measurands of the medium are to be measured and/or the supplementary training data includes multiple supplementary spectra $I_k$ and the corresponding supplementary values $m_k$ of each measurand.

In these embodiments, the transfer model TM is preferably determined based on transfer model training data including predictions MP of the measurands determined with the universal model GM based on the supplementary spectra $I_k$ and the corresponding supplementary value $m_k$ of each measurand. This can be achieved in various ways.

As an example, in certain embodiments, for at least one or each measurement situation, the transfer model TM is, e.g., determined by, based on a detailed analysis of the transfer model training data, determining and providing an algorithm for calculating the measurement results MR of each measurand based on the predictions MP of the measurand(s) determined with the universal model GM based on measured spectra $I_m$ determined by the spectrometer(s) 100 employed in the respective measurement situation.

In certain embodiments, the analysis of the transfer model training data and/or the determination of the transfer model TM, e.g., includes, based on the transfer model training data, performing a multivariate analysis, a partial least squares regression, a support vector regression, and/or a principal component analysis of the predictions MP and/or a method step of quantitatively assessing interdependencies between the predictions MP of the measurand(s) and the corresponding supplementary values $m_k$ of each measurand.

In other embodiments, determining the transfer model TM, e.g., includes based on the transfer model training data training a neural network to determine the measurement results MR of the measurand(s) based on predictions MP determined with the universal model GM based on measured spectra $I_m$ determined in the respective measurement situation and determining the transfer model TM to be given by the trained neural network.

Considering that predictions MP determined with the universal model GM are considerably less complex than the spectra based on which they have been determined, and that the application-specific interrelations between the spectral values of the measured spectra $I_m$ and the corresponding values of the measurand(s) are already accounted for by the universal model GM, the design and the structure of the transfer model TM accounting for the circumstances prevailing in the respective measurement situation is much simpler than the design and the structure of the universal model GM. This provides the advantage that correspondingly little time, effort, and/or computing power is required to determine the transfer model TM for the respective measurement situation.

The simplicity of the transfer model TM further provides the advantage that little supplementary training data is needed to determine the transfer model TM such that a high measurement accuracy is achieved with the dedicated model LM including the universal model GM and the transfer model TM. As an example, in certain embodiments, the transfer model TM is, e.g., determined based on a limited number of supplementary spectra $I_k$, e.g., a limited number smaller or equal to 100, smaller or equal to 50, or even smaller or equal to 20 supplementary spectra $I_k$, and the corresponding supplementary values $m_k$ of each measurand.

In addition or as an alternative, in certain embodiments, for at least one or each measurement situation, the dedicated model LM, is e.g., determined based on a combination of the dedicated model determination methods described above in context with FIGS. 3 and 5. In these embodiments, the dedicated model LM is, e.g., determined as a model given by an adapted universal model $GM_{RG}$ determining adapted predictions $MP_{RG}$ of each measurand based on measured spectra $I_m$ determined by the spectrometer(s) 100 employed in the respective measurement situation and an adapted transformer $T_A$ determining the measurement results MR of the measurand(s) based on the adapted predictions $MP_{RG}$ determined with the adapted universal model $GM_{RG}$.

Figure 6:
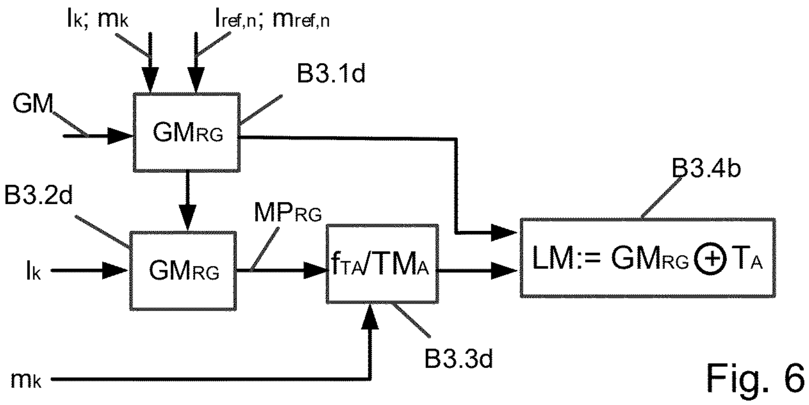
FIG. 6 shows a method of determining a dedicated model including an adapted universal model and an adapted transformer according to the present disclosure.

A corresponding embodiment of method step B3 of determining the dedicated model LM is shown in FIG. 6. As shown in FIG. 6, determining the dedicated model LM may include a method step B3.1*d* of determining the adapted universal model $GM_{RG}$ by, based on the universal model GM and the supplementary training data, retraining the universal model GM under consideration of the supplementary training data. Following the retraining, the adapted universal model $GM_{RG}$ is then determined to be given by the retrained universal model.

In analogy to the retraining method described in context with FIG. 3 above, in certain embodiments, retraining the universal model GM to account for the circumstances prevailing in the respective measurement situation is, e.g., performed in method step B3.1*d* shown in FIG. 6 in the same manner as the training of the universal model GM based on the same underlying algorithm that has previously been employed to determine the universal model GM.

As outlined above, retraining the universal model GM provides the advantage that different weights can be assigned to the universal training data and the supplementary training data. In the method shown in FIG. 3, the retrained universal model $GM_{RL}$ is subsequently employed as the dedicated model LM. Correspondingly, in context of the method shown in FIG. 3, the flexibility given by the assignment of different weights is preferably used as outlined above to strengthen the impact of the circumstances prevailing in the respective measurement situation on the retrained universal model $GM_{RL}$. In a contrast to that method, in the method shown in FIG. 6, the retrained universal model GM is subsequently employed as the adapted universal model $GM_{RG}$ constituting only a part of the dedicated model LM here additionally including the adapted transformer $T_A$. Correspondingly, in context of the method shown in FIG. 6, the flexibility given by assigning different weights is preferably used in a manner preserving the global validity of the resulting retrained universal model. As an example, in certain embodiments, method step B3.1*d* shown in FIG. 6 of retraining the universal model GM is, e.g., performed in a manner preserving the global validity of the resulting retrained universal model by assigning a smaller weight to the supplementary training data than to the universal training data.

Following the determination of the adapted universal model $GM_{RG}$, the determination of the dedicated model LM shown in FIG. 6 further includes the determination of the adapted transformer $T_A$. Determining the adapted transformer $T_A$, e.g., includes a method step B3.2*d* of, based on at least one or each supplementary spectrum $I_k$, with the adapted universal model $GM_{RG}$ determining the corresponding adapted prediction $MP_{RG}$ of each measurand, and a method step B3.3*d* of, based on the adapted predictions $MP_{RG}$ determined with adapted universal model $GM_{RG}$ based on the or each supplementary spectrum $I_k$ and the corresponding supplementary value(s) $m_k$ of the measurand (s), determining the adapted transformer $T_A$.

In analogy to the determination of the transformer T performed in method step B3.2*c* shown in FIG. 5, the adapted transformer $T_A$, is e.g., determined such that the measurement result MR of each measurand determined with the adapted transformer $T_A$ based on the adapted prediction $MP_{RG}$ determined with the adapted universal model $GM_{RG}$ based on the or each supplementary spectrum $I_k$ corresponds to the supplementary value $m_k$ of the respective measurand exhibited by the medium during the determination of the respective supplementary spectrum $I_k$.

In further analogy to the determination of the transformer T performed in method step B3.2*c* shown in FIG. 5, in certain embodiments, for at least one or each measurement situation determining the adapted transformer $T_A$, e.g., includes for each measurand determining an adapted transfer function $f_{TA}$ for calculating measurement results MR of the respective measurand as a function of the adapted prediction $MP_{RG}$ of the respective measurand and a set of at least one parameter. In this embodiment, the adapted transfer function $f_{TA}$ for each measurand is, e.g., determined as a linear function, a polynomial function of a given order, or another mathematical function for calculating measurement results MR of the respective measurand as a function of the adapted prediction $MP_{RG}$ of the respective measurand and a set of at least one parameter. For each measurand, the at least one parameter of the adapted transfer function $f_{TA}$ is, e.g., determined by fitting the respective adapted transfer function $f_{TA}$ to a set of at least one or multiple data points, wherein each data point is given by one of the adapted predictions $MP_{RG}$ of the respective measurand determined with the adapted universal model $GM_{RG}$ based on one of the supplementary spectra $I_k$ and the corresponding supplementary value $m_k$. To this extent, regression methods and/or polynomial fitting methods known in the art are, e.g., employed.

In addition or as an alternative, in certain embodiments, for at least one or each measurement site, the adapted transformer $T_A$, is e.g., determined in form of an adapted transfer model $TM_A$ for determining the measurement results MR based on the adapted predictions $MP_{RG}$ determined with the adapted universal model $GM_{RG}$ based on measured spectra $I_m$ determined by the spectrometer(s) 100 employed in the respective measurement situation. In these embodiments, the adapted transfer model $TM_A$ is preferably determined based on transfer model training data, including the adapted predictions $MP_{RG}$ of the measurand(s) determined with the adapted universal model $GM_{RG}$ based on the supplementary spectra $I_k$ and the corresponding supplementary values $m_k$.

As an example, in certain embodiments, the adapted transfer model $TM_A$ is, e.g., determined by, based on a detailed analysis of the transfer model training data, determining and providing an algorithm for calculating the measurement results MR of each measurand based on the adapted predictions $MP_{RG}$ of the measurand(s) determined with the adapted universal model $GM_{RG}$ based on measured spectra $I_m$ determined by the spectrometer(s) 100 employed in the respective measurement situation.

In certain embodiments, the analysis of the transfer model training data and/or the determination of the adapted transfer model $TM_A$, e.g., includes performing a multivariate analysis, a partial least squares regression, a support vector regression, and/or a principal component analysis of the adapted predictions $MP_{RG}$ and/or a method step of quantitatively assessing interdependencies between the adapted predictions $MP_{RG}$ of the measurands and the corresponding supplementary values $m_k$ of each measurand.

In other embodiments, determining the adapted transfer model $TM_A$, e.g., includes based on the transfer model training data training a neural network to determine the measurement results MR of the measurand(s) based on adapted predictions $MP_{RG}$ determined with the adapted universal model $GM_{RG}$ based on measured spectra $I_m$ determined in the respective measurement situation and determining the adapted transfer model $TM_A$ to be given by the trained neural network.

Regardless of the method employed to determine the dedicated model LM, in certain embodiments, for at least one or each measurement situation the method may further include an optional method step C1 of, based on the supplementary training data determined in the respective measurement situation and the dedicated model LM determined for the respective measurement situation, determining a measurement accuracy ΔMR of measurement results MR of each measurand determined with the dedicated model LM in the respective measurement situation.

As shown in FIG. 1, in certain embodiments, the optional method step C1, e.g., includes based on at least one or each supplementary spectrum $I_k$ with the dedicated model LM, determining a measurement result MR of each measurand and, based on the measurement result(s) MR determined based on the supplementary spectra $I_k$ and the corresponding supplementary values $m_k$, determining the measurement accuracy ΔMR of the measurement results MR achieved with the dedicated model LM.

The thus determined measurement accuracy ΔMR may be used in various ways. As an example, in certain embodiments, the method, e.g., includes an optional method step C2 of providing the measurement accuracy ΔMR.

In addition or as an alternative, the measurement accuracy ΔMR may be employed to ensure a predetermined minimum accuracy K, e.g., a minimum accuracy predetermined for at least one measurement site within the respective measurement situation, where spectrometric measurements are going to be performed. In these embodiments, the previously determined dedicated model LM is preferably only employed when the measurement accuracy ΔMR is higher or equal to the predetermined minimum accuracy K and an alternative solution is preferably employed in case the measurement accuracy ΔMR is lower than the predetermined minimum accuracy K. This alternative solution may be achieved in various ways.

As an example, in certain embodiments, for at least one measurement situation the measurement accuracy ΔMR achieved with the dedicated model LM may be improved by performing the method steps of determining additional supplementary training data and redetermining the dedicated model LM based on the supplementary training data and the additional supplementary training data. In this context, as indicated by the dotted arrows P1 and P2 shown in FIG. 1 the determination of the additional supplementary training data is, e.g., performed as outlined above in context with method steps B1 and/or B2. Redetermining the dedicated model LM is, e.g., performed by repeating method step B3 of determining the dedicated model LM based on the supplementary training data and the additional supplementary training data. Following this, the dedicated model LM for the respective measurement situation is then determined to be given by the redetermined dedicated model.

In addition or as an alternative, in certain embodiments, for at least one measurement situation the measurement accuracy ΔMR achieved with the dedicated model LM may be improved by performing the method steps of limiting the respective measurement situation to be given by a limited measurement situation predetermined by specifying at least one additional influencing factor affecting measured spectra $I_m$ determined by the spectrometer(s) in the respective measurement situation. In this embodiment, the method, e.g., further includes, based on the universal model GM and supplementary training data determined in the limited measurement situation, determining the dedicated model for determining measurement results of each measurand based on measured spectra $I_m$ of the medium determined and provided by the spectrometer(s) 100 employed in the limited measurement situation. In this respect, the determination of the supplementary training data and the determination of the dedicated model for the limited measurement situation is, e.g., performed as described above in context with method steps B1, B2 and B3.

Regardless of the method employed to determine the dedicated model LM, following the determination of the dedicated model LM, the sequence of method steps performed for each measurement situation according to the present disclosure further includes a method step B4 of, based on measured spectra $I_m$ of the medium determined and provided by the spectrometer(s) 100 employed in the respective measurement situation and the dedicated model LM, determining and providing measurement results MR of the or each measurand of the medium.

In each measurement situation, having measurement results MR determined with the corresponding dedicated model LM provides the advantage that of being more accurate than the predictions MP determined with the universal model GM. In this respect, the highest measurement accuracy is achieved with dedicated models LM determined for measurement situations that have been predetermined in a restrictive manner.

As shown in FIG. 2, in certain embodiments, the measurement results MR are, e.g., determined by an evaluation unit 17 connected to or communication with the signal processor 15 providing the measured spectra $I_m$. The evaluation unit 17 is, e.g., a computer, a microprocessor or another type of calculating unit determining and providing the measurement results MR based on the measured spectra $I_m$ and the dedicated model LM for determining the measurement result MR that has previously been determined. The exemplary evaluation unit 17 shown in FIG. 2 is, e.g., a component of the spectrometer 100 performing the spectroscopic measurements or a component of a measurement system including the at least one or each spectrometer 100 employed in the measurement situation(s) and the evaluation unit 17 connected to or communicating with the spectrometer(s) 100.

In a further embodiment, when the method shown in FIG. 1 is performed for at least two or more different measurement situations, supplementary training data that has previously been determined in method step B2 for at least one measurement situation may be used to increase the global validity of the universal model GM. In such an embodiment, the method further includes at least once performing a method step indicated by the arrow P3 shown in FIG. 1 of updating the universal model GM based on the universal training data and the supplementary training data that has previously been determined in method step B2 for at least one measurement situation. Updating the universal model GM is, e.g., performed in the same manner as the initial training of the universal model GM and/or based on the same underlying algorithm that has previously been employed to determine the universal model GM. In that case, the initial training of the universal models GM and the updating of the universal model GM differ in that the initial training is performed solely based on the universal training data, whereas the updating is performed based on the universal training data and previously determined supplementary training data. Updating the universal model GM is preferably performed in a manner increasing the global validity of the updated universal model GM. This is, e.g., attained by treating the supplementary training data as additional universal training data that is used in addition to and in the same manner as the initial universal training data.

Following the update, the updated universal model is then used as the universal model GM. In this respect, the method according to the present disclosure further includes for at least one further measurement situation determining the corresponding dedicated model LM as described above based on the updated universal model GM.

Each of the signal processor 13 and evaluation unit 17, and other units according to the present disclosure, may be a portion of a processing subsystem that includes one or more computing devices having memory, processing, and/or communication hardware. Each may be a single device or a distributed device, and the functions of each may be performed by hardware and/or software. Each may include one or more arithmetic logic units (ALUs), central processing units (CPUs), memories, limiters, conditioners, filters, format converters, or the like which are not shown to preserve clarity. In at least one embodiment, one or more of the signal processor 13 and evaluation unit 17 are programmable to execute algorithms and process data in accordance with operating logic that is defined by programming instructions, such as software or firmware. Alternatively or additionally, operating logic for the units may be at least partially defined by hardwired logic or other hardware, for example, using an application-specific integrated circuit (ASIC) of any suitable type. Each may be exclusively dedicated to the functions described herein or may be further used in the regulation, control, and activation of one or more other subsystems or aspects of the analyzers and spectrometers of the present disclosure.

While various embodiments of an analyzer and methods for using and constructing the same have been described in considerable detail herein, the embodiments are merely offered by way of non-limiting examples of the disclosure described herein. It will therefore be understood that various changes and modifications may be made, and equivalents may be substituted for elements thereof, without departing from the scope of the disclosure. The present disclosure is not intended to be exhaustive or to limit the scope of the subject matter of the disclosure.

Further, in describing representative embodiments, the disclosure may have presented a method and/or process as a particular sequence of steps. However, to the extent that the method or process does not rely on the particular order of steps set forth herein, the method or process should not be limited to the particular sequence of steps described. Other sequences of steps may be possible and thus remain within the scope of the present disclosure.

We claim:

1. A spectrometric measurement method of, in one measurement situation or in multiple different measurement situations within a predetermined application with at least one spectrometer of a predetermined type, determining measurement results of at least one measurand of a medium of an application specific type, wherein each measurement situation is predetermined by specifying at least one influencing factor affecting measured spectra determined by the spectrometer(s) in the respective measurement situation, the method comprising:

performing reference measurements by, with the at least one spectrometer, determining reference spectra of reference samples of the medium and, for each reference sample, determining and/or providing a reference value of each measurand of the reference sample;

based on universal training data, including the reference spectra and the corresponding reference values, determining a universal model for determining predictions of each measurand based on measured spectra of the medium determined by spectrometers in the predetermined application; and for each measurement situation:

in the respective measurement situation with the at least one spectrometer, determining and providing measured spectra of the medium;

for at least one supplementary spectrum or a limited number of supplementary spectra, wherein each supplementary spectrum is given by one of the measured spectra determined by the spectrometer(s) in the respective measurement situation, determining and/or providing a supplementary value of each measurand of the medium;

based on the universal model and supplementary training data including at least one or each supplementary spectrum and the corresponding supplementary value(s), determining a dedicated model for determining measurement results of each measurand based on measured spectra of the medium determined and provided by the spectrometer(s) employed in the respective measurement situation; and based on measured spectra of the medium determined and provided by the spectrometer(s) employed in the respective measurement situation and the dedicated model, determining and providing measurement results of each measurand of the medium.

2. The method according to claim 1, wherein each dedicated model is determined such that measurement results of each measurand determined with the dedicated model based on the or each supplementary spectrum correspond to the supplementary value of the respective measurand exhibited by the medium during the determination of the respective supplementary spectrum.

3. The method according to claim 1, wherein, for at least one or each measurement situation, determining the dedicated model comprises:

based on the universal model and the supplementary training data, retraining the universal model under consideration of the supplementary training data; and determining the dedicated model to be given by the retrained universal model.

4. The method according to claim 3, wherein retraining the universal model:

is performed in the same manner as the training of the universal model and/or based on the same underlying algorithm that has previously been employed to determine the universal model; and/or includes strengthening an impact of circumstances prevailing in the respective measurement situation on the retrained universal model by assigning a larger weight to the supplementary training data than to the universal training data.

5. The method according to claim 1, wherein, for at least one or each measurement site, determining the dedicated model comprises:

based on the supplementary training data, adjusting the universal model such that measurement results of each measurand determined with the adjusted universal model based on the supplementary spectra correspond to the supplementary values of the respective measurand exhibited by the medium during the determination of the respective supplementary spectrum; and determining the dedicated model to be given by the adjusted universal model.

6. The method according to claim 5, wherein adjusting the universal model comprises:

based on each supplementary spectrum, with the universal model determining the prediction of each measurand;

based on the predictions determined based on the supplementary spectra and the corresponding supplementary values, determining prediction errors exhibited by the predictions; and at least one of:

based on the prediction errors, adjusting the universal model such that prediction errors of predictions determined with the adjusted universal model based on the supplementary spectra are minimized;

based on the prediction errors, iteratively adjusting the universal model and repeating the method steps of, based on each supplementary spectrum, with the adjusted universal model determining the prediction of each measurand, determining prediction errors exhibited by these predictions, and subsequently adjusting the previously adjusted universal model until the prediction errors of predictions determined with the resulting adjusted universal model decrease below a predetermined threshold; and adjusting the universal model by adjusting at least one weighing factor, at least one parameter, a filter, a smoothing algorithm, and/or at least one other model component of the universal model such that deviations between predictions determined with the adjusted universal model based on the supplementary spectra and the corresponding supplementary values are minimized.

7. The method according to claim 1, wherein for at least one or each measurement site:

the dedicated model is determined as a model given by the universal model determining predictions of each measurand based on measured spectra determined by the spectrometer(s) employed in the respective measurement situation and a transformer determining measurement results of the measurand(s) based on the predictions determined with universal model; and determining the dedicated model includes:

based on at least one or each supplementary spectrum, with the universal model determining the corresponding prediction of each measurand; and based on the prediction(s) determined based on the or each supplementary spectrum and the corresponding supplementary value(s), determining the transformer such that the measurement result of each measurand determined with the transformer based on the prediction(s) determined with the universal model based on the or each supplementary spectrum corresponds to the corresponding supplementary value of the respective measurand exhibited by the medium during determination of the respective supplementary spectrum.

8. The method according to claim 7, wherein, for at least one or each measurement site, the transformer is determined by, for each measurand, determining a transfer function for calculating measurement results of the respective measurand as a function, as a linear function, a polynomial function of a given order, or another mathematical function of the prediction of the respective measurand and a set of at least one parameter, wherein:

for each measurand, the at least one parameter of the transfer function is determined by fitting the respective transfer function to a set of data points;

each data point is given by one of the predictions of the respective measurand determined with the universal model based on one of the supplementary spectra and the corresponding supplementary value; and the set of data points consists of a single data point, of two data points, of a limited number of data points smaller or equal to 20, smaller or equal 10 or even smaller or equal 5 data points, or of multiple data points.

9. The method according to claim 7, wherein for at least one or each measurement site:

the transformer included in the dedicated model is determined in form of a transfer model for determining measurement results of the measurand(s) based on predictions determined with the universal model based on measured spectra determined by the spectrometer(s) employed in the respective measurement situation; and determining the respective dedicated model includes, based on transfer model training data including predictions of the measurands determined with the universal model based on the supplementary spectra and the corresponding supplementary value(s) of each measurand, determining and providing the transfer model.

10. The method according to claim 9, wherein, for at least one or each measurement site, determining the transfer model comprises either at least one of:

a) based on a detailed analysis of the transfer model training data, determining and providing an algorithm for calculating the measurement results of each measurand based on predictions of the measurand(s) determined with the universal model based on measured spectra determined by the spectrometer(s) employed in the respective measurement situation; and b) based on the transfer model training data, performing a multivariate analysis, a partial least squares regression, a support vector regression, and/or a principal component analysis of the predictions and/or quantitatively assessing interdependencies between the predictions of the measurands and the corresponding supplementary values of each measurand; or based on the transfer model training data, training a neural network to determine the measurement results of the measurand(s) based on predictions determined with the universal model based on measured spectra determined in the respective measurement situation and determining the transfer model to be given by the trained neural network.

11. The method according to claim 9, wherein, for at least one or each measurement situation, the transfer model is determined based on supplementary training data including a limited number smaller or equal to 100, smaller or equal to 50 or even smaller or equal to 20 of supplementary spectra and the corresponding supplementary values.

12. The method according to claim 1, wherein for at least one or each measurement site:

the dedicated model is determined as a model given by an adapted universal model determining adapted predictions of each measurand based on measured spectra determined in the respective measurement situation and an adapted transformer determining the measurement results of the measurand(s) based on adapted predictions determined with the adapted universal model based on measured spectra determined in the respective measurement situation; and determining the dedicated model includes:

based on the universal model and the supplementary training data, retraining the universal model under consideration of the supplementary training data and determining the adapted universal model to be given by the retrained universal model;

based on at least one or each supplementary spectrum, with the adapted universal model determining the adapted prediction of each measurand; and based on the adapted prediction(s) determined with the adapted universal model based on the or each supplementary spectrum and the corresponding supplementary value(s), determining the adapted transformer such that the measurement result of each measurand determined with the adapted transformer based on the adapted prediction(s) determined with the adapted universal model based on the or each supplementary spectrum corresponds to the supplementary value of the respective measurand exhibited by the medium during the determination of the respective supplementary spectrum.

13. The method according to claim 12, wherein determining the adapted universal model comprises retraining of the universal model:

in the same manner as the training of the universal model and/or based on the same underlying algorithm previously employed to determine the universal model; and/or in a manner preserving a global validity of the retrained universal model by assigning a smaller weight to the supplementary training data than to the universal training data.

14. The method according to claim 12, wherein determining the adapted transformer comprises, for each measurand, determining an adapted transfer function for calculating measurement results of the respective measurand as a function, as a linear function, a polynomial function of a given order, or another mathematical function of the adapted prediction of the respective measurand and a set of at least one parameter, wherein for each measurand the at least one parameter of the adapted transfer function is determined by fitting the respective adapted transfer function to a set of at least one or multiple data points, wherein each data point is given by one of the adapted predictions of the respective measurand determined with the adapted universal model based on one of the supplementary spectra and the corresponding supplementary value.

15. The method according to claim 12, wherein, for at least one or each measurement site, the adapted transformer is determined in form of an adapted transfer model for determining measurement results of the measurand(s) based on adapted predictions of the measurand(s) determined with the adapted universal model based on measured spectra determined in the respective measurement situation, and wherein the adapted transfer model is determined based on transfer model training data including the adapted predictions of the measurand(s) determined with the adapted universal model based on the supplementary spectra and the corresponding supplementary values.

16. The method according to claim 15, wherein determining the adapted transfer model comprises either at least one of:

a) based on a detailed analysis of the transfer model training data, determining and providing an algorithm for calculating measurement results of each measurand based on adapted predictions of the measurand(s) determined with the adapted universal model based on measured spectra determined in the respective measurement situation; and b) performing a multivariate analysis, a partial least squares regression, a support vector regression, and/or a principal component analysis of the adapted predictions and/or quantitatively assessing interdependencies between the adapted predictions of the measurand(s) and the corresponding supplementary values of each measurand; or based on the transfer model training data, training a neural network to determine the measurement results of the measurand(s) based on the adapted predictions determined with the adapted universal model based on the measured spectra determined in the respective measurement situation and determining the adapted transfer model to be given by the trained neural network.

17. The method according to claim 15, wherein, for at least one or each measurement situation, specifying the at least one influencing factor includes at least one of:

specifying at least one influencing factor associated with a measurement set-up;

specifying the measurements to be performed on samples of the medium or to be in situ measurements;

specifying the measurements to be performed in a flow-cell conducting the medium or a in container, a bioreactor or another type of vessel containing the medium;

specifying at least one influencing factor associated with measurement conditions;

specifying a parameter range for at least one parameter and/or a temperature;

specifying at least one influencing factor associated with the medium of the application-specific type within the respective measurement situation;

specifying at least one property of the medium;

specifying the medium to being subjected to a specified process, a specified production process and/or a specified processing procedure;

specifying a facility containing and/or processing the medium;

specifying the medium to include at least one specified component, to include multiple specified components, or to consist of specified components;

specifying the specific spectrometer performing the measurements; and specifying the specific measurement site where the measurements are performed.

18. The method according to claim 1, wherein:

the predetermined application is a biotechnological application, wherein mammalian cells producing an active component of a drug are grown in a cell culture medium; and at least one measurement situation is predetermined by specifying or by solely specifying the type of the cell culture medium and/or the type of the mammalian cells.

19. The method according to claim 1, further comprising for at least one or each measurement situation:

based on the supplementary training data and the dedicated model, determining a measurement accuracy of measurement results determined with the dedicated model; and performing at least one of:

a) providing the measurement accuracy; and b) when the measurement accuracy is lower than a predetermined minimum accuracy:

determining additional supplementary training data, redetermining the dedicated model based on the supplementary training data and the additional supplementary training data, and determining the dedicated model to be given by the redetermined dedicated model; and/or limiting the respective measurement situation to be given by a limited measurement situation predetermined by specifying at least one additional influencing factor affecting measured spectra determined by the spectrometer(s) in the respective measurement situation and, based on the universal model and supplementary training data determined in the limited measurement situation, determining the dedicated model for determining measurement results of each measurand based on measured spectra of the medium determined and provided by the spectrometer(s) employed in the limited measurement situation.

20. The method according to claim 1, further comprising at least one of:

updating the universal model based on the universal training data and the supplementary training data previously determined for at least one measurement situation at least once; and subsequently, for at least one measurement situation, determining the corresponding dedicated model based on the updated universal model at least once.

* * * * *